(12) United States Patent
Hou et al.

(10) Patent No.: US 9,408,685 B2
(45) Date of Patent: Aug. 9, 2016

(54) APPLICATOR FOR SELF-EXPANDING INTRAVAGINAL URINARY INCONTINENCE DEVICES

(71) Applicant: FIRST QUALITY HYGIENIC, INC., Great Neck, NY (US)

(72) Inventors: Mari Hou, Basking Ridge, NJ (US); Raymond J. Hull, Jr., Hampton, NJ (US); Alan Trojanowski, Monmouth Junction, NJ (US)

(73) Assignee: First Quality Hygienic, Inc., Great Neck, NY (US)

( * ) Notice: Subject to any disclaimer, the term of this patent is extended or adjusted under 35 U.S.C. 154(b) by 66 days.

(21) Appl. No.: 13/771,728

(22) Filed: Feb. 20, 2013

(65) Prior Publication Data
US 2013/0165843 A1    Jun. 27, 2013

Related U.S. Application Data

(62) Division of application No. 12/609,139, filed on Oct. 30, 2009.

(51) Int. Cl.
*B29C 45/16* (2006.01)
*A61F 2/00* (2006.01)
(Continued)

(52) U.S. Cl.
CPC .............. *A61F 2/005* (2013.01); *A61F 13/2097* (2013.01); *A61F 13/26* (2013.01); *A61F 13/266* (2013.01); *B29C 2045/1678* (2013.01)

(58) Field of Classification Search
CPC ............ A61F 13/2097; B29C 45/1676; B29C 2045/1678
USPC ................................................. 264/250, 255
See application file for complete search history.

(56) References Cited

U.S. PATENT DOCUMENTS 3,706,311 A   12/1972   Kokx et al.
4,019,498 A    4/1977   Hawtrey et al.
(Continued)

FOREIGN PATENT DOCUMENTS

CN          101522140 A        9/2009
DE         202006004901        7/2006
(Continued)

OTHER PUBLICATIONS

Zhanxiong L et al., entitled "High Temperature Resistant Polymers," Chemical Industry Press, 2007, 3 pages.
(Continued)

*Primary Examiner* — Jill Heitbrink
(74) *Attorney, Agent, or Firm* — Amster, Rothstein & Ebenstein LLP

(57) ABSTRACT

An applicator for a self-expanding intravaginal device has a barrel and a plunger that can substantially contain the self-expanding intravaginal device without significant insertion barrel distortion while maintaining comfortable applicator insertion. The barrel has an insertion end, an opposed gripper end, and a central portion therebetween, and it is arranged and configured to substantially contain the self-expanding intravaginal device. The plunger is in telescoping relation with the barrel, and it is arranged and configured to expel the self-expanding intravaginal device out of the insertion end of the barrel when the plunger is pushed into the gripper end of the barrel. A plurality of flexible petals substantially closes the insertion end of the barrel, and the central portion of the barrel has a load to 3 mm deflection of at least about 15 Newtons. Other aspects of the invention include a self-expanding intravaginal urinary incontinence system, and methods of making the applicator.

8 Claims, 2 Drawing Sheets

(51) Int. Cl.
*A61F 13/20* (2006.01)
*A61F 13/26* (2006.01)

(56) References Cited

U.S. PATENT DOCUMENTS

| | | | |
|---|---|---|---|
| 4,048,998 A | 9/1977 | Nigro | |
| 4,125,113 A | 11/1978 | Morman et al. | |
| 4,320,751 A | 3/1982 | Loeb | |
| 4,347,209 A * | 8/1982 | Suzuki | 264/250 |
| 4,444,711 A * | 4/1984 | Schad | 264/243 |
| 4,677,967 A | 7/1987 | Zartman | |
| 4,743,422 A | 5/1988 | Kalriis-Nielsen et al. | |
| 5,501,063 A | 3/1996 | Tews et al. | |
| 5,681,894 A | 10/1997 | Williams et al. | |
| 5,928,183 A | 7/1999 | Fox et al. | |
| 5,997,467 A | 12/1999 | Connolly | |
| 6,035,238 A | 3/2000 | Ingle et al. | |
| 6,183,681 B1 | 2/2001 | Sullivan et al. | |
| 6,312,419 B1 | 11/2001 | Durel-Crain | |
| 6,460,542 B1 | 10/2002 | James | |
| 6,530,879 B1 | 3/2003 | Adamkiewicz | |
| 6,702,281 B2 | 3/2004 | Post et al. | |
| 6,752,950 B2 * | 6/2004 | Clarke | 264/255 |
| 6,958,057 B2 * | 10/2005 | Berg, Jr. et al. | 604/385.17 |
| 7,163,554 B2 | 1/2007 | Williams et al. | |
| 7,250,129 B2 | 7/2007 | Williams et al. | |
| 7,717,892 B2 | 5/2010 | Bartning et al. | |
| 7,862,533 B2 * | 1/2011 | LeMay et al. | 604/11 |
| 7,910,126 B2 | 3/2011 | Ahmed et al. | |
| 9,050,183 B2 | 6/2015 | Bartning et al. | |
| 2004/0249352 A1 | 12/2004 | Swick | |
| 2005/0125020 A1 | 6/2005 | Meade et al. | |
| 2006/0213918 A1* | 9/2006 | Rajala et al. | 221/33 |
| 2007/0156080 A1 | 7/2007 | Loyd et al. | |
| 2007/0203429 A1 | 8/2007 | Ziv | |
| 2007/0244352 A1 | 10/2007 | Ziv | |
| 2008/0009662 A1 | 1/2008 | Bartning et al. | |
| 2008/0009663 A1 | 1/2008 | Bartning et al. | |
| 2008/0009664 A1 | 1/2008 | Bartning et al. | |
| 2008/0009666 A1 | 1/2008 | Bartning et al. | |
| 2008/0009814 A1 | 1/2008 | Bartning et al. | |
| 2008/0009931 A1 | 1/2008 | Bartning et al. | |
| 2008/0033230 A1 | 2/2008 | Bartning et al. | |
| 2008/0033231 A1 | 2/2008 | Bartning et al. | |
| 2008/0033337 A1* | 2/2008 | Dougherty et al. | 604/15 |
| 2008/0188924 A1 | 8/2008 | Prabhu | |
| 2008/0234831 A1 | 9/2008 | Clarke et al. | |
| 2008/0243046 A1 | 10/2008 | Cettina et al. | |
| 2009/0247929 A1 | 10/2009 | Hou et al. | |
| 2010/0016780 A1 | 1/2010 | VanDenBogart et al. | |
| 2010/0164139 A1* | 7/2010 | LeMay et al. | 264/296 |
| 2012/0136199 A1 | 5/2012 | Hou et al. | |
| 2013/0160272 A1 | 6/2013 | Bartning et al. | |
| 2013/0165742 A1 | 6/2013 | Bartning et al. | |
| 2013/0211185 A1 | 8/2013 | Hull, Jr. et al. | |

FOREIGN PATENT DOCUMENTS

| | | |
|---|---|---|
| EP | 1 837 151 A1 | 9/2007 |
| EP | 2106769 A | 10/2009 |
| JP | 2007185914 | 7/2007 |
| WO | 2005087154 A2 | 9/2005 |
| WO | WO 2007/146270 A | 12/2007 |
| WO | 2008008794 A2 | 1/2008 |
| WO | 2009/079607 * | 6/2009 |

OTHER PUBLICATIONS

Wang X et al., entitled "Performance, Polymerization and Spinning of Polyetherimide," Materials Review (2007), 11 pages.

Zhou K et al., entitled "Characteristics, Processing and Application of Polyetherimide," Technology and Materials, 2003, 5 pages.
Omnexus, entitled "Hardness of different families of thermoplastic elastomers," internet archive capture from Nov. 7, 2007.
Office Action dated Apr. 22, 2015 in connection with U.S. Appl. No. 11/456,390.
Office Action dated Aug. 12, 2015 in connection with U.S. Appl. No. 12/609,139.
Office Action dated Feb. 10, 2015 in connection with U.S. Appl. No. 12/609,139.
Office Action dated Jun. 24, 2015 in connection with U.S. Appl. No. 12/956,824.
Office Action dated Aug. 17, 2015 in connection with U.S. Appl. No. 11/456,402.
Russian Office Action in connection with Russian Patent Application No. 2012131356, filed Dec. 21, 2010, Decision on Grant.
Japanese Office Action dated Mar. 27, 2015 in connection with Japanese Patent Application No. 2012-546153, Notification of Reasons for Refusal (w/English Translation).
Chinese Office Action dated Dec. 16, 2014 in connection with Chinese Patent Application No. 201180057634.5, Notice of the First Office Action (w/English Translation).
Chinese Office Action dated Feb. 27, 2015 in connection with Chinese Patent Application No. 201280027261.1, Notification of the First Office Action (w/English Translation).
Office Action dated May 23, 2012 in connection with U.S. Appl. No. 12/645,800—non-final rejection.
Guo Y et al., entitled "Isothermal physical aging characterization of Polyether-ether-ketone (PEEK) and Polyphenylene sulfide (PPS) films by creep and stress relaxation," Mech Time-Depend Mater (2007) 11: 61-89.
Office Action dated Dec. 26, 2014 in connection with U.S. Appl. No. 12/956,824.
Office Action dated Jun. 3, 2015 in connection with U.S. Appl. No. 11/776,178.
Office Action dated Feb. 17, 2015 in connection with U.S. Appl. No. 11/776,178.
Office Action dated Apr. 3, 2015 in connection with U.S. Appl. No. 12/959,582.
Decision to Grant and Translation in Russian Patent Application No. 2013129826 issued Aug. 28, 2015.
Office Action dated Oct. 6, 2015 in connection with U.S. Appl. No. 11/456,390.
Office Action dated Oct. 2, 2015 in connection with U.S. Appl. No. 12/956,824.
Office Action dated Oct. 30, 2015 in connection with U.S. Appl. No. 12/959,582.
Office Action dated Feb. 2, 2016 in connection with U.S. Appl. No. 12/059,774.
Office Action dated May 11, 2016 in connection with U.S. Appl. No. 11/456,390.
Chinese Office Action dated Nov. 30, 2015, Notice on the First Office Action, in connection with Chinese Patent Application No. 201410520637.3.
Office Action dated Jan. 25, 2016 in connection with U.S. Appl. No. 11/456,390.
Office Action dated Jan. 20, 2016 in connection with U.S. Appl. No. 13/881,838.
Communication Pursuant to Article 94(3) EPC dated Feb. 22, 2016 in connection with European Patent Application No. 07812764.4, 4 pages.
Office Action dated Apr. 7, 2016 in connection with U.S. Appl. No. 12/609,139.
Office Action dated Mar. 11, 2016 in connection with U.S. Appl. No. 12/956,824.
Australian Office Action dated Apr. 12, 2016 in connection with Australian Patent Application No. 2015201997.

* cited by examiner

APPLICATOR FOR SELF-EXPANDING INTRAVAGINAL URINARY INCONTINENCE DEVICES

This application is a divisional of U.S. application Ser. No. 12/609,139 filed Oct. 30, 2009, the complete disclosure of which is hereby incorporated herein by reference for all purposes.

FIELD OF THE INVENTION

The present invention relates to an applicator suitable for intravaginal devices. The applicator is useful for placing the device in the vagina in the correct position to enable the device to function. The applicator is designed to be used with self-expanding intravaginal urinary incontinence devices.

BACKGROUND OF THE INVENTION

Tampons are absorbent articles that are inserted into a woman's vagina to absorb blood and other menstrual discharges. Intravaginal urinary incontinence devices are inserted into a woman's vagina to reduce or inhibit urinary incontinence. Applicators may be used to ease the insertion of both urinary incontinence devices and tampons. Applicators typically include a generally cylindrical barrel for holding the tampon or device and placing in the vagina. The barrel may also include what are commonly called petals at the insertion end. Petals are flexible flaps that go from a "closed" or rounded configuration to an "open" configuration which allows the contained tampon or device to be expelled from the barrel. The applicator also includes a plunger for expelling the device or tampon into the vagina. Cardboard and plastic applicators are known in the art. Typically, disposable plastic applicators are utilized to deliver tampons inside the vagina. Disposable applicators for tampons typically utilize a single plastic resin construction. However some tampon applicators have considered the use of combinations of plastic materials. For example, Williams et al., U.S. Pat. No. 5,681,894, describes a tampon applicator barrel made up of linear low density polyethylene and styrene-butadiene-styrene block copolymer to provide comfort and ease of insertion.

However, the physical characteristics of some intravaginal urinary incontinence devices vary significantly from tampons. In particular, self-expanding intravaginal urinary incontinence devices may exert significant forces on the applicator containing them, so the choice of materials used to make the applicators may be significantly restricted.

Intravaginal incontinence devices are designed to exert significant pressure within a user's vagina to support an adjacent urinary system. Prior to use, the device may be contained within an applicator for delivery into a vagina. Therefore, designers have had to modify the intravaginal urinary incontinence devices to minimize the distorting forces that may be exerted upon the device applicator. For example, Ziv, US Pub. Pat. App. 2007/0203429 discloses an intravaginal urinary incontinence device that must be "activated" or manually expanded after insertion to provide the force necessary to support the urinary system.

Alternately, the applicator strength must be increased to oppose the distorting forces of a self-expanding intravaginal urinary incontinence device. Because such a device may be in a constricted configuration, it is important that the applicator be able to withstand the pressure exerted by the incontinence device over an extended period of time (prior to use). However, such a modification may make it difficult or impossible to provide a closed insertion end with petals that are flexible enough to permit the expulsion of the device without too much force.

Thus, there is a continuing need for a self-expanding intravaginal urinary incontinence device that is structurally strong enough to avoid distortion or deformation over an extended period of time in storage prior to use, yet have soft, flexible petals for comfortable insertion.

SUMMARY OF THE INVENTION

Surprisingly, we have found that an applicator for a self-expanding intravaginal device having a barrel and a plunger can substantially contain the self-expanding intravaginal device without significant insertion barrel distortion while maintaining comfortable applicator insertion. The barrel has an insertion end, an opposed gripper end, and a central portion therebetween, and it is arranged and configured to substantially contain the self-expanding intravaginal device. The plunger is in telescoping relation with the barrel, and it is arranged and configured to expel the self-expanding intravaginal device out of the insertion end of the barrel when the plunger is pushed into the gripper end of the barrel. A plurality of flexible petals substantially closes the insertion end of the barrel, and the central portion of the barrel has a load to 3 mm deflection of at least about 15 Newtons.

In another aspect of the invention a self-expanding intravaginal urinary incontinence system includes a self-expanding intravaginal urinary incontinence device and an applicator substantially containing the self-expanding intravaginal urinary incontinence device. The applicator has a plunger in telescoping relation with a barrel having an insertion end, an opposed gripper end, and a central portion therebetween. A plurality of flexible petals substantially closes the insertion end of the barrel, and the central portion of the barrel has a load to 3 mm deflection of at least about 15 Newtons.

In another aspect of the invention a method of making an insertion barrel for an applicator for a self-expanding intravaginal device includes the steps of:
  a. forming a first mold cavity configuration corresponding to a first section comprising the insertion end of the insertion barrel;
  b. injecting a first, flexible polymeric material into the first mold cavity configuration;
  c. forming a second mold cavity configuration to permit overmolding a second, relatively rigid polymeric material onto the first section;
  d. injecting the second, relatively rigid polymeric material into the second mold cavity configuration to form a second section of the insertion barrel extending from the first section, wherein the second section comprises a central portion and gripper portion of the insertion barrel; and
  e. ejecting the insertion barrel from the second mold cavity configuration.

In yet another aspect of the invention a method of making an insertion barrel for an applicator for a self-expanding intravaginal device includes the steps of:
  a. injecting a first, flexible polymeric material into a first mold cavity to form a first section comprising the insertion end of the insertion barrel;
  b. ejecting the first section of the insertion barrel from the first mold;
  c. injecting a second, relatively rigid polymeric material into a second mold cavity to form a second section comprising a central portion and gripper portion of the insertion barrel;

d. ejecting the second section of the insertion barrel from the second mold;

e. attaching the second section to the first section to form the insertion barrel.

BRIEF DESCRIPTION OF THE DRAWINGS

The invention will be more fully understood and further advantages will become apparent when reference is made to the following detailed description of the invention and the accompanying drawings in which.

DETAILED DESCRIPTION OF PREFERRED EMBODIMENTS

The present invention relates to self-expanding intravaginal urinary incontinence system that includes a self-expanding intravaginal urinary incontinence device and an applicator for delivering the device. The applicator includes a barrel to substantially contain the device and a plunger in telescoping relation with the barrel to expel the device from the insertion end of the barrel. Because the self-expanding intravaginal urinary incontinence device may exert significant forces on the applicator containing them, the choice of materials used to make the applicators may be significantly restricted. Further, materials useful to provide an applicator barrel that resists distortion caused by the force exerted by the incontinence device may be too stiff to provide a closed insertion end with petals that are flexible enough to permit the expulsion of the device without excessive force.

Therefore, it may be possible to provide an applicator barrel having sufficient rigidity with substantially thinned insertion end petals that are flexible enough for reasonable expulsion of the incontinence device. Alternatively, it may be necessary to employ different plastic material for portions of the applicator barrel. For example, a relatively rigid material may be used in a central portion of the barrel to withstand the forces exerted by the self-expanding intravaginal urinary incontinence device on the barrel, and another, relatively flexible material may be used to form the petals that substantially close the insertion end of the applicator barrel.

Figure 1:
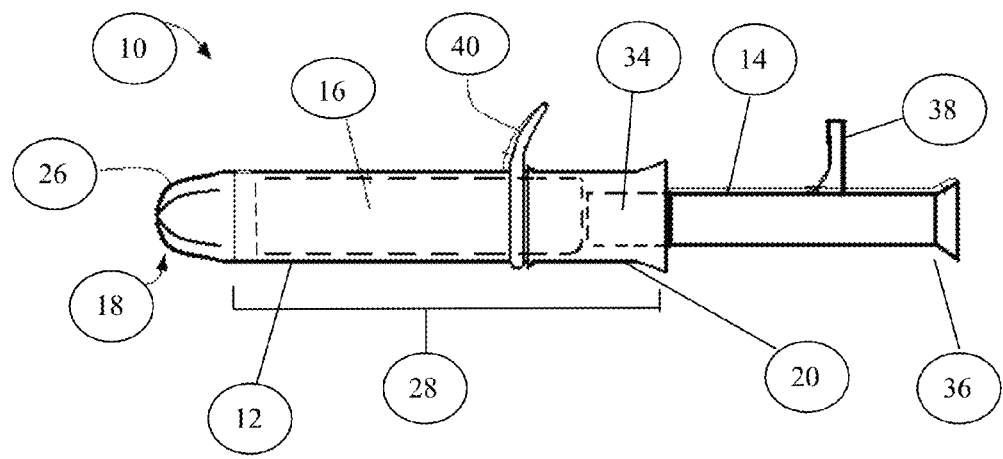
FIG. 1 is a side elevation of an applicator of the present invention.
Figure 2:
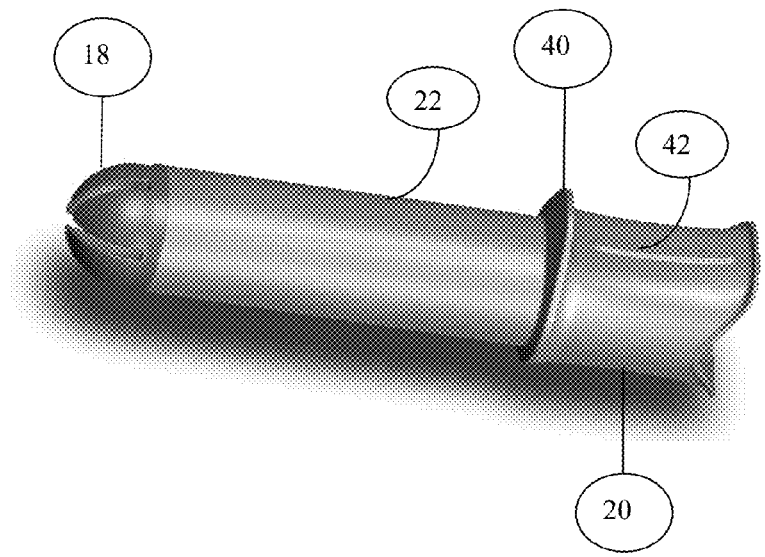
FIG. 2 is a perspective view of one embodiment of a two-component insertion barrel useful in an applicator of the present invention.
Figure 3:
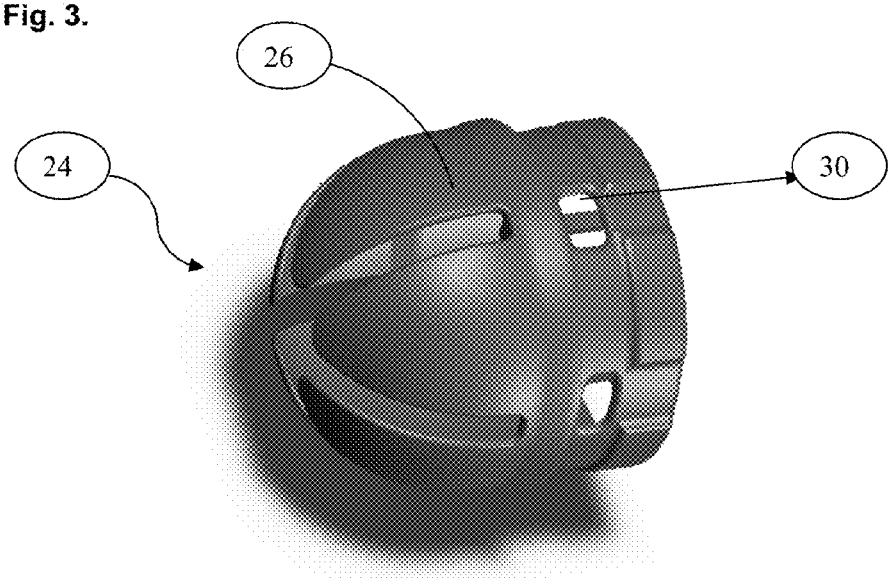
FIG. 3 is a perspective view of the first section of the insertion barrel of FIG. 2.
Figure 4:
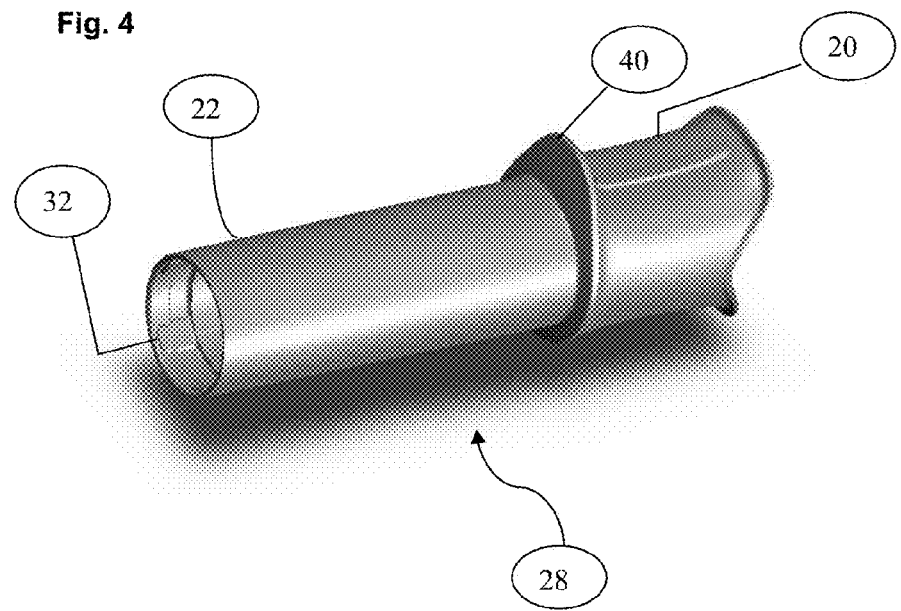
FIG. 4 is a perspective view of the second section end of the insertion barrel of FIG. 2.

Turning to the figures, FIG. 1 shows one embodiment of the present invention. Applicator 10 includes an elongate insertion barrel 12 and a plunger 14. The insertion barrel 12 is arranged and configured to substantially contain the self-expanding intravaginal urinary incontinence device 16. The insertion barrel has an insertion end 18, an opposed gripper end 20, and a central portion 22, therebetween. In the embodiment of FIGS. 2-4, the insertion barrel 12 includes a first section 24 including the insertion end 18 of the barrel 12. This section may be formed of a relatively flexible material to form the petals 26 that substantially close the insertion end 18 of the applicator barrel 12. A second section 28 including the gripper end 20 and the central portion 22 of the insertion barrel 12 abuts the first section 24. This second section 28 may be formed of a relatively rigid material to withstand the forces exerted by the self-expanding intravaginal urinary incontinence device 16.

The length of the barrel 12 may range from about 20 mm to 100 mm. The outer diameter of the barrel may range from about 5 mm to 25 mm for comfortable insertion into the vagina. The thickness of the barrel wall is sufficient to withstand the pressure exerted by the device, and may range, for example, from about 0.5 mm to 2 mm. The urinary incontinence device can be loaded into either end of the barrel prior to final assembly of the applicator 10. The insertion end 18 has petals 26 for easing insertion of the applicator and for retaining the device until deployment. In one embodiment of this invention, the first section 24, including the insertion end 18, is separate from the first section 24. In another embodiment, the first section 24 and the second section 28 are different materials but are integrally formed with no distinct parts, such as by overmolding.

As used herein, the terms "flexible material" shall mean a material that has a sufficient flexibility to permit easy expulsion of the contained self-expanding intravaginal urinary incontinence device from the applicator. A flexible material has a lower flexural modulus than the rigid material described below.

As used herein, the term "rigid material" shall mean a structural material that provides a central portion of the insertion barrel with sufficient stiffness to resist significant distortion under a load of a contained self-expanding intravaginal urinary incontinence device. A significant measure of the barrel stiffness is the "load to 3 mm deflection" as measured in the Barrel Stiffness Test described below.

Barrel Stiffness Test

The barrel stiffness test is used to determine the force required to compress an applicator barrel by a fixed distance of 3 mm, the "load to 3 mm deflection." The applicator barrel samples are prepared by cutting off the petals and finger grip end, creating a cylinder approximately 1.5-2" in length. The sample is then held between two 4×4" compression plates. The bottom plate is fixed at the base, and the other plate is attached to the moving crosshead. The top compression plate is brought down until it touches the sample. This is set as the zero position. The top plate compresses the sample by a distance of 3 mm, and at a rate of approximately 2 inches (50.8 mm) per minute, and the resistive force is recorded.

Three comparative tampon applicators were tested according to the Barrel Stiffness Test alongside two embodiments of the present invention. The results are shown in Table 1, below.

TABLE 1

| Samples (n = 5) | Wall Thickness (inches) | Outer Diameter (inches) | Average Force (N) |
| --- | --- | --- | --- |
| Comparative Product 1: Kotex ® Security ® Tampons | 0.02 | 0.75 (19 mm) | 6.3 |
| Comparative Product 2: Tampax ® Pearl Tampons | 0.032 | 0.62 (15.7 mm) | 8.1 |
| Comparative Product 3: Playtex ® Gentle Glide ® Tampons | 0.032 | 0.65 (16.5 mm) | 11.4 |
| Inventive Sample 1: White LLDPE with 2% Slip Agent | 0.05 | 0.71 (18 mm) | 48.3 |
| Inventive Sample 2: White LLDPE with 2% Slip Agent | 0.05 | 0.79 (20 mm) | 52.3 |

The three Comparative Products used were 1) Kotex® Security® Tampons, Super Plus Absorbency from Kimberly-Clark, Neenah, Wis., 2) Tampax® Pearl Tampons, Super Plus Absorbency from Procter & Gamble, Cincinnati, Ohio, and 3) Playtex® Gentle Glide® Super Plus Absorbency from Playtex Products, Dover Del.

The insertion barrel 12 preferably includes two different plastic materials—the first section 24 including the insertion end 18 and its petals 26 formed of a relatively flexible polymeric material—and the first section 24, comprised of a relatively rigid polymeric material. A representative, non-limiting list of useful flexible polymeric materials includes as Low Density Polyethylene (LDPE), Linear Low Density Polyethylene (LLDPE), Thermoplastic Elastomers (TPE) and combinations thereof. A representative, non-limiting list of useful rigid polymeric materials includes acrylonitrile-butadiene-styrene (ABS), High Density Polyethylene (HDPE), Linear Low Density Polyethylene (LLDPE), Polypropylene (PP), Polyamide (nylon or PA), Polyoxymethylene (POM), polystyrene, and combinations thereof.

Preferably, the flexible polymeric material has a lower flexural modulus than the relatively rigid polymeric material. This provides the flexibility useful to form comfortable petals in the first section and the stiffness useful to provide the rigidity in the central portion.

The rigid polymeric material provides a rigid central portion 22 of the insertion barrel 12. Preferably, the insertion barrel 12 has a load to 3 mm deflection of at least about 15 Newtons, more preferably at least about 20 Newtons, and most preferably, at east about 30 Newtons, and most, most preferably, at least about 40 Newtons.

FIGS. 2-4 shows in greater detail the barrel of the present invention. As previously mentioned, the barrel 12 can be formed of a first section 24 including the insertion end 18, which is then attached to the second section 28. One way of attaching the first and second sections 24, 28 is by way of mechanical fit. In the embodiment shown, holes 30 spaced away from the insertion end 18 engage protuberances 32 on the inner surface of the first section 24 to provide a mechanical fit between the two different sections. Other methods such as ultrasonic welding may also be used to secure the two sections together.

In another embodiment, the applicator barrel is made by two-step injection molding (or overmolding) of two different compatible polymeric materials to provide a secure attachment of the sections. In this process, a first shot of a flexible material, such as LDPE, is injected into a portion of a mold to form the first section 24 of the barrel 12 including the petals 26, and a second shot of a more rigid material, such as a LLDPE, is injected into a modified mold to form the first section 24 including the central portion 22 and finger grip end 20. In an alternate process, the first shot is of the more rigid material to form the central portion and finger grip end, and the second shot of the flexible material is overmolded to form the insertion end.

The following Table 2 provides compatibility pairings of different polymeric materials that deliver good adhesion between the components:

TABLE 2

Combinations of materials known in prior art showing good adhesion[1]

| | ABS | ASA | SAN | S/B | PS | PMMA | PC | PSU | HDPE | LDPE | PP | EVA | PA 6 | PA 66 | POM | PBT | S/B- | PC- | PBT |
|---|---|---|---|---|---|---|---|---|---|---|---|---|---|---|---|---|---|---|---|
| ABS | + | + | + | − | − | + | + | + | − | − | − | | + | + | | + | − | + | + |
| ASA | + | + | + | − | − | + | + | + | − | − | − | | + | + | | + | − | + | + |
| SAN | + | + | + | − | − | + | + | | − | − | − | | | | | + | − | + | + |
| S/B | − | − | − | + | + | − | − | | − | − | − | | | | − | − | + | o | o |
| PS | − | − | − | + | + | − | − | | − | − | − | + | − | − | − | − | + | o | o |
| PMMA | + | + | + | − | − | + | o | | o | o | − | | | | | | | + | + |
| PC | + | + | + | − | − | o | + | + | − | − | − | o | | | | + | o | + | + |
| PSU | + | + | | | | + | + | | | | | | | | | | o | + | + |
| HDPE | − | − | − | − | − | o | − | | + | + | + | + | o | o | o | − | o | o | o |
| LDPE | − | − | − | − | − | o | − | | + | + | + | + | o | o | o | − | o | o | o |
| PP | − | − | − | − | − | − | − | | + | + | + | + | o | o | o | − | o | o | o |
| EVA | | | | − | + | | | | + | + | + | + | | | | | o | o | o |
| PA 6 | + | + | | − | − | | o | | o | o | o | o | + | + | | | o | + | + |
| PA 66 | + | + | | − | − | | o | | o | o | o | o | + | + | | | o | + | + |
| POM | | | | − | − | | | | o | o | o | | | | + | | o | o | o |
| PBT | + | + | + | − | − | + | − | | − | − | − | | | | | + | − | + | + |
| PPE + S/B | − | − | − | + | + | | o | o | o | o | o | o | o | o | o | − | + | o | o |
| ABS + PC | + | + | + | o | o | + | + | o | o | o | o | o | + | + | o | + | o | + | + |
| PC + PBT | + | + | + | o | o | + | + | | − | − | − | − | + | + | o | + | − | + | + |

+ = good adhesion   o = poor adhesion   − = no adhesion

[1]Designing for production, 7.2 Cooling and solidification, Pg 275-309. Hanser Publishers, Copyright © 2006.

ABS—Acrylonitrile-Butadiene-Styrene
ASA—Acrylonitrile - Styrene - Acrylate
SAN—Styrene-Acrylonitrile
S/B−
PS—Polystyrene
PMMA—Polymethyl Methacrylate
PC—Polycarbonate
PSU—Polysulfone
HDPE—High Density Polyethylene
LDPE—Low Density Polyethylene
PP—Polypropylene
EVA—Ethylene vinyl acetate
PA6—Polyamide 6
PA66—Polyamide 66
POM—Polyoxymethylene
PBT—Polybutylene terephthalate
PPE + S/B−
ABS + PC−
PC + PBT−

Applicators according to the present invention also include a deployment plunger 14, an elongate device designed to fit in a telescoping manner within the barrel 12. The plunger 14 has a leading end 34 to bear against and to deploy the incontinence device 16 and an opposite end 36 having a stop 38 to prevent the plunger from being pushed too far and to ensure proper placement of the device in the vagina. The plunger 14 is moved axially into the insertion barrel 12 in a telescoping manner to deploy the device 16 from the insertion end 18 into the vagina. The plunger 14 may be made from any suitable material. For example, the plunger may be molded from conventional thermoplastic materials such as, but not limited to, polyethylene (including without limitation HDPE, LDPE, LLDPE, etc.), polypropylene and a variety of copolymers. It is important that the plunger be strong enough to expel the incontinence device from the barrel without buckling.

An insertion depth indicator 40 (shown FIGS. 2 and 3) may be a raised element on the insertion barrel surface, oriented generally perpendicular to the longitudinal axis of the insertion barrel (and thus, the direction of insertion). This provides a tactile feedback when the insertion is completed. The height of the insertion depth indicator may range from 2 mm to 20 mm. The insertion depth indicator may be made from any suitable material, such as polyethylene, polypropylene, a variety of copolymers, silicone, and elastomeric materials, such as ethylene propylenediene monomer and the like. The insertion depth indicator may be molded into the barrel or may be formed separately and attached to the applicator through conventional methods, such as adhesives, friction fits and the like. The insertion depth indicator is positioned such that the device is deployed in the proper position within the vagina.

Applicators according to the present invention may also include an orientation indicator 42 (also shown in FIGS. 2-3). The orientation indicator 42 may be helpful to place the incontinence device 16 in the vagina such that when it is deployed, the portion of the device that applies pressure, exerts pressure on the urethro-vesical junction, and any anchoring members lie on the lateral sides of the vagina. The orientation indicator 42 may clearly mark the orientation of the device within the applicator 10. The indicator 42 may be a raised line, a colored line, dots, embossments, or any suitable mark or shape that indicates orientation. The orientation indicator may be on any or all of a conventional finger grip, the insertion depth indicator, and the barrel 12 itself. If the device is aligned with the orientation indicator when it is within the applicator, then it will be aligned to the body after insertion. When the orientation indicator 42 is part of the insertion depth indicator 40, the orientation indicator 42 may be part of the shape of the insertion depth indicator 40.

Suitable urinary incontinence devices for use with the applicators of the present invention include, but are not limited to, devices taught in co-pending US Patent Applications, US Publication No. 20080009662 A1; US Publication No. 20080033230 A1; US Publication No. 20080009931 A1; US Publication No. 20080009814 A1; US Publication No. 20080009663 A1; US Publication No. 20080033231 A1; US Publication No. 20080009664 A1; and US Publication No. 20080009666 A1.

Examples are set forth below to further illustrate the nature of the invention and the manner of carrying it out. However, the invention should not be considered as being limited to the details thereof.

EXAMPLE 1

The second section of the barrel according to FIG. 2 was molded out of polypropylene (PP) and the first section including the insertion end and the petals according to FIG. 4, was molded out of low-density polyethylene (LDPE). Deployment plunger according to FIG. 1 was molded out of linear low-density polyethylene (LLDPE) with a 1% modified polyethylene slip additive. The petals were then affixed onto the barrel using conventional mechanical fastening methods. The collar and finger grip components also utilized single cavity injection molds. A finger-grip sleeve and the insertion depth indicator collar were both designed to be friction fit attached to the applicator. The material utilized was a 65-durometer thermoplastic elastomer under the trade name of C-flex. The collar and the finger grip were both fit to the barrel such that they could be slid to different positions on the barrel that were associated with a woman's depth of labia associated with her BMI (Body Mass Index).

Samples of the barrel and petals were also molded using different polymeric materials as given in the table below.

TABLE 3

Different combinations used to make the main portion of the barrel and insertion end.

| Barrel | Petals |
|---|---|
| PP | LDPE |
| HDPE | LDPE |
| LLDPE | LDPE |
| PP | TPE |
| HDPE | TPE |
| LLDPE | TPE |
| LLDPE | LLDPE |

In addition, some of the products were stored with self-expanding intravaginal urinary incontinence devices formed of nitinol as taught in co-pending US Patent Applications, US Publication No. 20080009662 A1; US Publication No. 20080033230 A1; US Publication No. 20080009931 A1; US Publication No. 20080009814 A1; US Publication No. 20080009663 A1; US Publication No. 20080033231 A1; US Publication No. 20080009664 A1; and US Publication No. 20080009666 A1, the disclosures of which are hereby incorporated by reference.

After accelerated aging (Aging conditions: 40° C./75% RH), ovality measurements were made. The following Table 4 provides the measurement results for the second section of the insertion barrel made using different polymeric materials.

TABLE 4

Ovality at the end of 4 weeks for different polymeric materials used to make the main body portion of the barrel.

| Polymeric material | Top ovality | Middle ovality | Bottom ovality |
|---|---|---|---|
| LLDPE | 2.4 | 0.53 | 2.22 |
| HDPE | 2.04 | 0.38 | 0.98 |
| PP | 1.18 | 0.22 | 0.62 |
| LDPE | 1.2 | 0.56 | 0.4 |

Thus, it can be seen that the selected materials provide minimal distortion due to the internal pressures of self-expanding intravaginal urinary incontinence devices.

Consumer Use Test

A use test was performed with 23 women to evaluate the level of comfort of the applicator of the 2-component applicator product. In the study, the women were given the applicator, lubrication (KY® Jelly), and a set of insertion and removal instructions. The women inserted the applicator after reading the instructions and then removed the applicator, leaving the tampon product inside their body. The tampon product was used in replacement for the intravaginal incontinence device. The women then filled out a questionnaire about the applicator (comfort, ergonomics, petal pinching, etc.). A one-on-one interview was then conducted to review their comments.

The results of this study are shown in Table 5 below.

TABLE 5

Parameters tested for evaluating consumer comfort

| Sr. No. | Parameters tested | No. of consumers that agreed | No. of consumers that disagreed |
|---|---|---|---|
| 1. | While inserting, this applicator is comfortable | 23 | 0 |
| 2. | While inserting, the tip of this applicator is comfortable | 23 | 0 |
| 3. | While insertion, the tube of this applicator is comfortable | 23 | 0 |
| 4. | Throughout the insertion process, I have experienced pinching | 0 | 22 |
| 5. | Throughout the insertion, I have experienced discomfort | 0 | 22 | n = 23

Based on the data above, it was determined that the 2-component applicator was comfortable while inserting and the women did not experience pinching or discomfort.

The specification and embodiments above are presented to aid in the complete and non-limiting understanding of the invention disclosed herein. Since many variations and embodiments of the invention can be made without departing from its spirit and scope, the invention resides in the claims hereinafter appended.

We claim:

1. A method of making an insertion barrel for an applicator for a self-expanding intravaginal device comprising the steps of:
   a. forming a first mold cavity configuration corresponding to a first section comprising a plurality of flexible petals at the insertion end of the insertion barrel;
   b. injecting a first, flexible polymeric material into the first mold cavity configuration;
   c. forming a second mold cavity configuration to permit overmolding a second, polymeric material which is rigid relative to the flexible polymeric material onto the first section;
   d. injecting the second, relatively rigid polymeric material into the second mold cavity configuration to form a second section of the insertion barrel extending from the first section, wherein the second section comprises a central portion and gripper portion of the insertion barrel; and
   e. ejecting the insertion barrel from the second mold cavity configuration,
   wherein the flexible polymeric material has a lower flexural modulus than the relatively rigid polymeric material.

2. The method of claim 1, wherein the flexible polymeric material is selected from the group consisting of low density polyethylene, linear low density polyethylene, thermoplastic elastomer, and combinations thereof.

3. The method of claim 1, wherein the relatively rigid polymeric material is selected from the group consisting of acrylonitrile-butadiene-styrene, high density polyethylene, linear low density polyethylene, polypropylene, polyamide, polyoxymethylene, polystyrene, and combinations thereof.

4. The applicator of claim 1, wherein the central portion of the barrel made has a load to 3 mm deflection of at least about 15 Newtons.

5. A method of making an insertion barrel for an applicator for a self-expanding intravaginal device comprising the steps of:
   a. forming a first mold cavity configuration corresponding to a first section comprising a central portion and gripper portion of the insertion barrel;
   b. injecting a first, polymeric material which is rigid relative to a second flexible polymeric material into the first mold cavity configuration;
   c. forming a second mold cavity configuration to permit overmolding the second, flexible polymeric material onto the first section;
   d. injecting the second, flexible polymeric material into the second mold cavity configuration to form a second section of the insertion barrel extending from the first section, wherein the second section comprises a plurality of flexible petals at an insertion end of the insertion barrel; and
   e. ejecting the insertion barrel from the second mold cavity configuration,
   wherein the flexible polymeric material has a lower flexural modulus than the relatively rigid polymeric material.

6. The method of claim 5, wherein the flexible polymeric material is selected from the group consisting of low density polyethylene, linear low density polyethylene, thermoplastic elastomer, and combinations thereof.

7. The method of claim 5, wherein the relatively rigid polymeric material is selected from the group consisting of acrylonitrile-butadiene-styrene, high density polyethylene, linear low density polyethylene, polypropylene, polyamide, polyoxymethylene, polystyrene, and combinations thereof.

8. The applicator of claim 5, wherein the central portion of the barrel made has a load to 3 mm deflection of at least about 15 Newtons.

* * * * *